United States Patent [19]

Nylen

[11] 4,352,374

[45] Oct. 5, 1982

[54] APPARATUS FOR DILUTING A CONCENTRATED SOLUTION

[75] Inventor: Ulf T. G. Nylen, Lund, Sweden

[73] Assignee: Gambro AB, Sweden

[21] Appl. No.: 121,873

[22] Filed: Feb. 15, 1980

Related U.S. Application Data

[63] Continuation of Ser. No. 855,603, Nov. 29, 1978, abandoned.

[30] Foreign Application Priority Data

Nov. 29, 1976 [SE] Sweden .................... 7613374

[51] Int. Cl.³ .............................................. E03B 7/07
[52] U.S. Cl. .......................... 137/564.5; 137/101.11;
137/205.5; 128/214 E; 128/DIG. 13
[58] Field of Search ............. 137/564.5, 101.11, 205.5;
128/213 A, 214 F, 214 E, 214 R, DIG. 12,
DIG. 13, 214 B

[56] References Cited

U.S. PATENT DOCUMENTS

| 2,332,157 | 10/1943 | Mapson | 128/214 R |
|---|---|---|---|
| 2,487,348 | 11/1949 | Malsbary | 137/101.11 |
| 3,225,759 | 12/1965 | Drapen | 137/564.5 X |
| 3,489,145 | 1/1970 | Judson | 128/214 R |
| 3,512,517 | 5/1970 | Kadish | 128/214 R |
| 3,590,845 | 7/1971 | MacLean | 137/564.5 X |
| 3,709,222 | 1/1973 | DeVries | 128/213 A |
| 3,712,511 | 1/1973 | Magnasco | 137/101.11 X |
| 3,812,482 | 5/1974 | Clark | 128/DIG. 13 X |
| 3,832,998 | 9/1974 | Gregg | 128/DIG. 13 X |

Primary Examiner—Harold W. Weakley
Attorney, Agent, or Firm—Lerner, David, Littenberg & Samuel

[57] ABSTRACT

An apparatus and method are provided for diluting a concentrated solution to be analyzed which includes a Y-coupling for combining a diluent and the concentrated solution to form a mixture. The mixture is then divided into first and second parts, such as by a pumping arrangement, with the second part of the mixture being proportional in quantity to the quantity of concentrated solution. The first part of the mixture is then supplied to an analytical device for analyzing the mixture. A chamber including a movable wall element is provided which divides the chamber into two subchambers. The first part of the mixture is supplied to the subchamber on one side of the movable wall element, which causes the movable wall element to force a proportional quantity of diluent out of the subchamber on the other side of the movable wall element. The dispensed diluent is then conveyed to mix with the concentrated solution.

5 Claims, 2 Drawing Figures

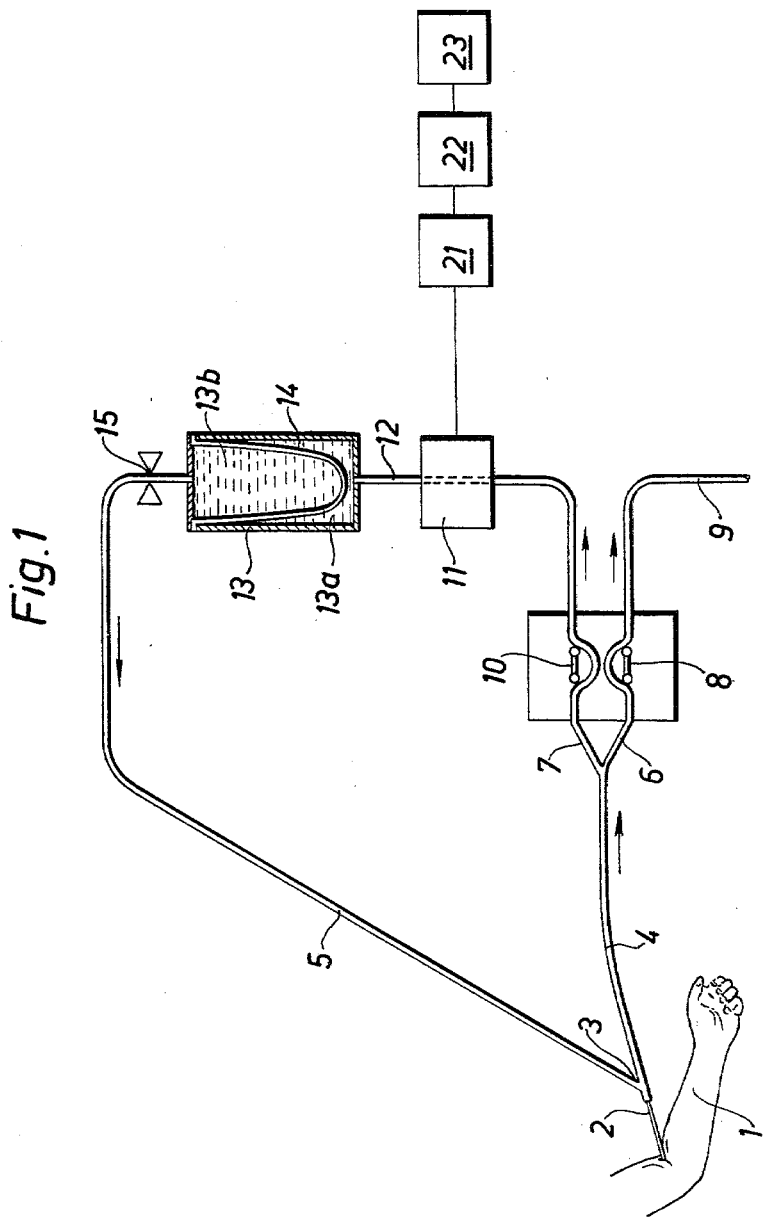

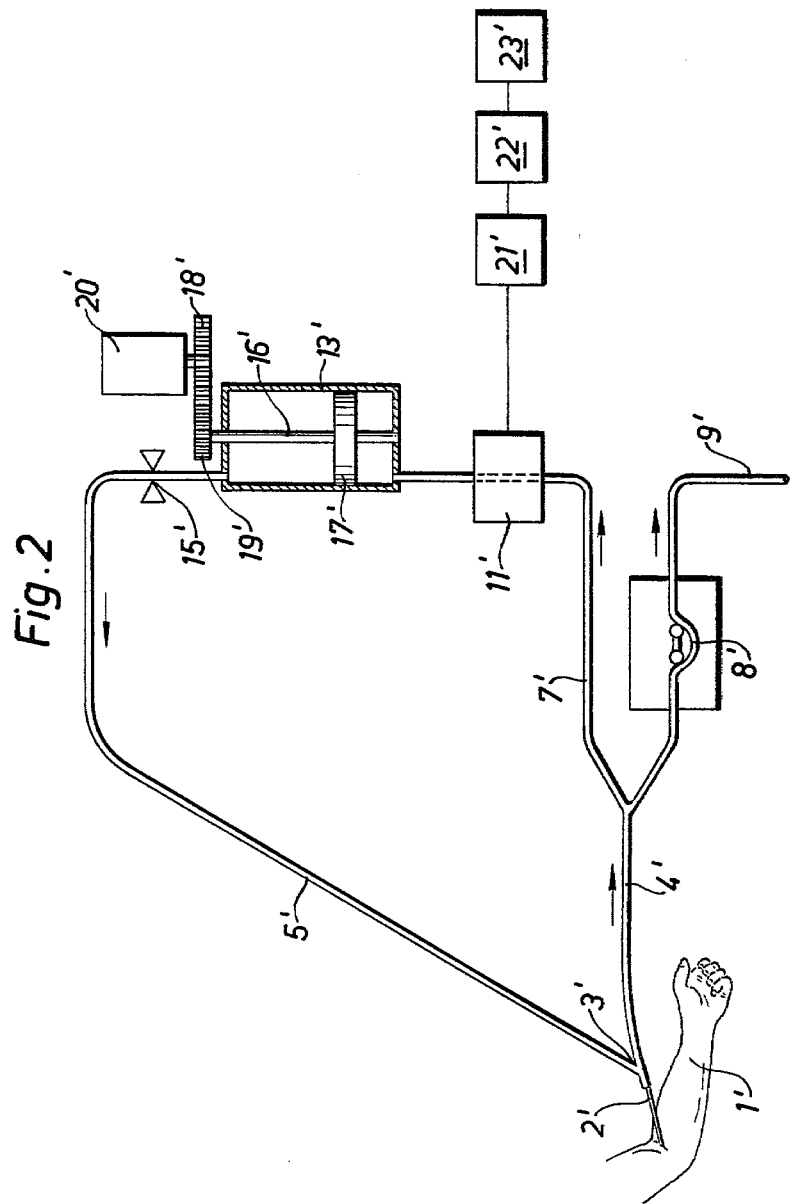

APPARATUS FOR DILUTING A CONCENTRATED SOLUTION

This is a continuation of application Ser. No. 855,603, filed Nov. 29, 1978, now abandoned.

FIELD OF THE INVENTION

The present invention relates generally to a method and apparatus for diluting a concentrated solution to be analyzed in such a manner that standard pumps may be employed.

BACKGROUND OF THE INVENTION

In systems in which small quantities of concentrated solution are to be diluted with a large quantity of a diluent, if two pumps of different capacities are employed for the concentrated solution and diluent, then any error in the pump for the diluent may detrimentally affect the outcome. Such a situation can be particularly dangerous when the concentrated fluid being diluted is blood and is being taken continuously from a patient. If the pump for the diluent is not a precision pump having a small degree of error, the result could be that diluted mixture is pumped into the patient.

In addition, if the concentrated solution to be diluted is blood, it coagulates over a relatively short distance, so that it is advantageous if the dilution of the blood can take place near its source.

Accordingly, it is an object of the present invention to provide an improved method and apparatus which overcomes one or more of the aforesaid problems. Specifically, it is within the contemplation of the present invention to provide an improved method and apparatus for diluting a concentrated solution, such as blood, wherein standard pumps may be employed, and their normal range of error will not detrimentally affect the process.

It is a further object of the present invention to provide an improved method and apparatus wherein the dilution of the concentrated solution takes place near the source of the concentrated solution, such as blood, so that the pumps and other equipment may be placed at a relatively large distance from the source of the concentrated solution.

SUMMARY OF THE INVENTION

Briefly, in accordance with the principles of the present invention, an improved method and apparatus is provided for diluting a concentrated solution, such as blood, so that it may be analyzed. A Y-coupling is provided for combining the diluent and the concentrated solution to form a mixture. A pair of pumps is provided to divide the mixture into first and second parts, with the second part being proportional in quantity to the quantity of concentrated solution which is supplied to form the mixture. The first part of the mixture is then pumped to analytical apparatus, and from there, it is supplied to a chamber which dispenses diluent from the chamber proportional in quantity to the quantity of the mixture received. The dispensed diluent is then conveyed to mix with the concentrated solution at the Y-coupling.

In one embodiment, the chamber includes a movable wall element separating the chamber into first and second subchambers so that as the first subchamber receives the first part of the mixture, it forces the movable wall element to move and to dispense diluent from the second subchamber in a proportional or equal amount. In an alternative embodiment, the chamber and movable wall element can take the form of a piston and cylinders.

Advantageously, as a result of the present invention, the dilution of the concentrated solution, such as blood, takes place near the source of the blood. As a result, the present invention eliminates problems with various fluids, such as blood or fluids having a low rate of flow, since problems of coagulation and the like are avoided which could operate to clog up the conduits of the system. Additionally, as a result of the present invention, the pumps and other equipment, such as the analytical equipment, may be placed at a relatively large distance from the source of the concentrated solution, such as blood. Advantageously, as a result of the present invention, the dilution takes place before the fluids enter the pumps, so that the time and distance of transport of the concentrated solution, such as blood, is relatively short.

In addition, the present invention is also advantageous as compared to a system wherein the dilution is carried out by pumping the diluent to a dilution point, and from there, by means of a second pump, the diluted solution is pumped to a point of analysis. In such arrangements, the pumps would have to be very accurate in order for the error tolerance to be acceptable. For example, if an error tolerance of approximately 10 percent is acceptable in the analysis, and the dilution is 50 times, the error tolerance of each of the pumps could not be greater than 0.1 percent. However, pumps of such precision are very expensive. Advantageously, as a result of the present invention, it is possible to use standard pumps, which are much less expensive and which have an error tolerance of about 5 percent.

As noted above, as the diluted mixture is intended primarily for use in connection with analysis, it should be combined with analytical equipment to receive the mixture before it is supplied to the chamber. This analytical equipment may, for example, be of the type which is described in U.S. patent application Ser. No. 755,977, filed on Dec. 30, 1976.

BRIEF DESCRIPTION OF THE DRAWINGS

Further objects, features, and advantages of the present invention will become apparent upon the consideration of the following detailed description of presently-preferred embodiments, when taken in conjunction with the accompanying drawings, wherein:

FIG. 1 diagrammatically illustrates apparatus for performing the method of the present invention; and FIG. 2 is an alternative arrangement diagrammatically illustrating apparatus for performing the method of the present invention.

DETAILED DISCUSSION OF PREFERRED EMBODIMENTS OF THE INVENTION

In the construction according to FIG. 1, blood is taken from a patient 1 through a preferably heparinized cannula 2. At a so-called Y-coupling 3, the blood is introduced into a conduit 4, and at the same time, it is mixed with a diluent from a conduit 5. The conduit 4 divides up into two branch conduits 6 and 7, the first named of which leads to an outlet 9 via a pump 8, while the latter leads to an analytical device 11 via a pump 10. From the analytical device 11, the mixture is conveyed via a conduit 12 to a rigid housing 13 which, by means of a membrane 14, is divided into subchamber 13a intended to receive the mixture, and subchamber 13b, containing a supply of diluent. This diluent is subsequently pressed out of subchamber 13b as the mixture is received in subchamber 13a. The diluent is pressed out by a restriction 15 into the conduit 5 and supplied to the Y-coupling to be mixed with the blood from the cannula 2.

If, for example, a mixing ratio of 1:70 is desired, the pump 8 is set, for example, at 1 ml/h, while the pump 10 is set at 69 ml/h. Assuming that the pumps are absolutely correct, the flow in the conduit 5 will then be 69 ml/h, and the flow in the conduit 4 will be 70 ml/h. From the patient 1 is drawn 1 ml/h. If there is an error in the pump 10, the quantities in the conduits 4 and 5 will be increased, but not the flow through the cannula 2 and the pump 8, since in the system described, the flow through the cannula 2 only depends on the pump 8 which can more easily be kept at a lower absolute error. If, for example, the error on both pumps 8 and 10 is about 5 percent, the absolute error of the pump 8 will only be 1/69 of the absolute error of pump 10.

Of course, pump 8 can be set to pump an amount which is proportional to the flow in cannula 2, and the quantity of fluid being conveyed through the system will either increase or decrease, depending on whether the flow in cannula 2 is higher or lower than the flow at outlet 9. Similarly, chamber 13 can be set to dispense an amount of diluent proportional to the incoming mixture 12, and this will cause the quantity of fluid conveyed through the system to increase or decrease.

The embodiment according to FIG. 2 corresponds in principle to that according to FIG. 1. The same reference designations have therefore been used but with the addition of a prime sign. The only difference is in the fact that the pump 10 and housing 13 have been eliminated and have been replaced by a cylinder 13' with a piston 17' driven on an axle 16'. This piston 17' may be driven, for example, by being provided with a female thread which engages with a corresponding thread on the axle 16' which may be driven by a motor 20' via gears 18' and 19'.

In the two arrangements described, the mixture to be examined is fed through an analytical device 11 and 11', respectively. This analytical unit may consist, for example, of an analytical electrode combined with an electrometer 21 and 21', respectively, which in turn is connected via a computer 22 and 22', respectively, to a control unit 23 and 23', respectively.

As mentioned above, this analysis may take place in substantially the same manner as that described in U.S. patent application Ser. No. 755,977, filed on Dec. 30, 1976. This analytical process is therefore not described in detail in the present patent application.

Naturally, the invention is not limited solely to the embodiments described above but can be varied within the scope of the following claims. For example, the components used in the respective systems may be varied within wide limits in respect of their shape as well as their function, without exceeding the scope of the invention. If, for example, the cannula 3 consists of a so-called double cannula, a first dilution of the blood can take place at the tip of this cannula. If the blood is then diluted with an equal quantity of heparin, a final blood concentration of 1:70 can be achieved by drawing 1 ml of blood and adding 1 ml heparin, then diluting this mixture with 68 ml of diluent. The pumps 8 and 10 in such a case are adapted to drawing or pumping 2 and 68 ml/h, respectively.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Apparatus for use in the continuous analysis of a mixture of a minor amount of a concentrated solution dissolved in a major amount of a diluent comprising a housing including adjacent first and second chambers separated from each other by a movable flexible wall membrane so that liquid in said first chamber cannot enter said second chamber, said second chamber including said diluent and said first chamber adapted to receive said mixture, said movable flexible wall membrane being adapted to move solely in response to said mixture being supplied to said first chamber so as to increase the volume of said first chamber and simultaneously decrease the volume of said second chamber, thereby expelling a proportionate amount of said diluent therefrom so that said diluent may be utilized to produce said mixture, supply means for supplying said mixture produced from said diluent to said first chamber, the total amount of said diluent comprising a predetermined fluid amount, concentrated solution supply means for supplying said concentrated solution at a predetermined rate, mixing means for mixing said diluent expelled from said second chamber with said concentrated solution supplied by said concentrated solution supply means so as to provide said mixture to be supplied to said first chamber, and removal means for withdrawing a portion of said mixture from said supply means at a rate proportional to said predetermined rate, whereby said predetermined fluid amount remains substantially constant.

2. The apparatus of claim 1 wherein said supply means and said removal means comprise a pair of pumps.

3. The apparatus of claim 1 including restriction means for restricting the flow of said diluent expelled from said second chamber of said housing.

4. The apparatus of claim 1 including analyzer means associated with said supply means for analyzing said mixture.

5. The apparatus of claim 1 wherein said concentrated solution comprises blood.

* * * * *